(12) United States Patent
Jin et al.

(10) Patent No.: US 8,927,565 B2
(45) Date of Patent: Jan. 6, 2015

(54) COMPOSITIONS FOR VETERINARY AND MEDICAL APPLICATIONS

(75) Inventors: Betty Jin, Mt Waverley Victoria (AU); Wen-Yang Wu, Mt Waverley Victoria (AU)

(73) Assignee: Australian Biomedical Company Pty. Ltd. (AU)

( * ) Notice: Subject to any disclaimer, the term of this patent is extended or adjusted under 35 U.S.C. 154(b) by 1145 days.

(21) Appl. No.: 10/570,509

(22) PCT Filed: Aug. 26, 2004

(86) PCT No.: PCT/AU2004/001151
§ 371 (c)(1),
(2), (4) Date: Feb. 28, 2006

(87) PCT Pub. No.: WO2005/020997
PCT Pub. Date: Mar. 10, 2005

(65) Prior Publication Data
US 2007/0027176 A1   Feb. 1, 2007

(30) Foreign Application Priority Data

Aug. 28, 2003  (AU) .................................. 2003904654
Sep. 4, 2003   (AU) .................................. 2003904817

(51) Int. Cl.

| | | |
|---|---|---|
| *A61K 31/4745* | (2006.01) | |
| *A61K 31/717* | (2006.01) | |
| *A23K 1/16* | (2006.01) | |
| *A23K 1/17* | (2006.01) | |
| *A23K 1/18* | (2006.01) | |
| *A23L 1/30* | (2006.01) | |
| *A61K 31/47* | (2006.01) | |
| *A61K 31/718* | (2006.01) | |
| *A61K 31/78* | (2006.01) | |

(52) U.S. Cl.
CPC ............. *A61K 31/717* (2013.01); *A23K 1/1625* (2013.01); *A23K 1/17* (2013.01); *A23K 1/1826* (2013.01); *A23K 1/184* (2013.01); *A23L 1/3002* (2013.01); *A61K 31/47* (2013.01); *A61K 31/718* (2013.01); *A61K 31/78* (2013.01)
USPC ........................................................ 514/284

(58) Field of Classification Search
CPC ..... A23K 1/1625; A23K 1/17; A23K 1/1826; A23K 1/184; A61K 2300/00; A61K 31/47; A61K 31/717; A61K 31/718; A61K 31/78
See application file for complete search history.

(56) References Cited

U.S. PATENT DOCUMENTS

| | | |
|---|---|---|
| 2,801,216 A | 7/1957 | Yoder et al. |
| 3,016,328 A | 1/1962 | Pepper et al. |
| 3,679,792 A | 7/1972 | Litchfield et al. |
| 4,034,084 A | 7/1977 | Siragusa |
| 5,409,903 A | 4/1995 | Polak et al. |
| 6,410,040 B1 | 6/2002 | Melrose et al. |

FOREIGN PATENT DOCUMENTS

| | | |
|---|---|---|
| AU | 2004267873 B2 | 2/2008 |
| AU | 2004267873 C1 | 12/2008 |
| CA | 2536489 A1 | 3/2005 |

(Continued)

OTHER PUBLICATIONS

Scher et al, "Effects of oxidized cellulose and microfibrillar collagen on infection," 1982, Surgery, 91(3), Abstract only.*

(Continued)

*Primary Examiner* — Kortney L Klinkel
(74) *Attorney, Agent, or Firm* — Joshua King; Constellation Law Group PLLC

(57) ABSTRACT

Compositions including polymeric dialdehydes and compounds of

Formula (1)

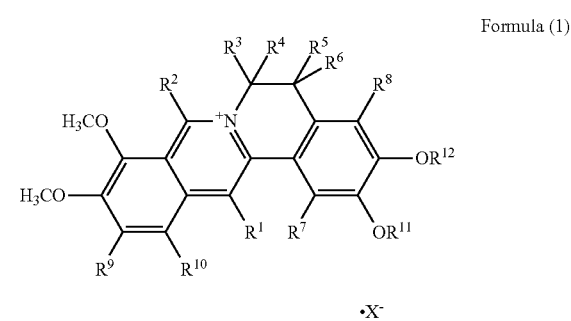

where $R^1$, $R^2$, $R^7$, $R^8$, $R^9$, and $R^{10}$ may be the same or different and are selected from H, $CH_3$, OH, $OCH_3$, $C_2H_5$, $OC_2H_5OCH_2Ph$, $OCH_2PhNO_2$, F or Cl;

$R^3$, $R^4$, $R^5$, $R^6$ may be the same or different and are selected from H, $CH_3$, $OCH_3$, $C_2H_5$, $OC_2H_5OCH_2Ph$, $OCH_2PhNO_2$, F or Cl, or $R^5$ and $R^6$ are the same or different and are selected from H, $CH_3$, $OCH_3$, $C_2H_5$, $OC_2H_5OCH_2Ph$, $OCH_2PhNO_2$, F or Cl and $R^3$ and $R^4$ together are =O, or $R^4$ and $R^6$ are the same or different and are selected from H, $CH_3$, $OCH_3$, $C_2H_5$, $OC_2H_5OCH_2Ph$, $OCH_2PhNO_2$, F or Cl and $R^3$ and $R^5$ together form a double bond or are =O, or $R^3$ and $R^4$, are the same or different and are selected from H, $CH_3$, $OCH_3$, $C_2H_5$, $OC_2H_5OCH_2Ph$, $OCH_2PhNO_2$, F or Cl and $R^5$ and $R^6$ together are =O;

$R^{11}$ and $R^{12}$ together form =$CH_2$, or $R^{11}$ and $R^{12}$ may be the same or different and are independently selected from the group consisting of H, $CH_3$, $CH_2CH_3$ and $CH_2CH_2CH_3$; and X is selected from the group consisting of Cl, Br, $SO_4$, I and $R^{13}COO$, where $R^{13}$ is $CH_3$ or poly acids, for the treatment of gastrointestinal functional disorders or related conditions as well as for the promotion of general health and weight gain in animals including humans.

23 Claims, No Drawings

(56) References Cited

FOREIGN PATENT DOCUMENTS

| CN | 1193471 A | 9/1998 |
|---|---|---|
| CN | 1845738 A | 10/2006 |
| EP | 1304041 A1 | 4/2003 |
| EP | 1663225 A1 | 6/2006 |
| JP | 62-01277 A | 1/1987 |
| JP | 62-012777 | 1/1987 |
| JP | 7504171 T | 5/1995 |
| JP | 09187229 | 7/1997 |
| JP | 2007504097 T | 3/2007 |
| WO | 9638186 | 12/1996 |
| WO | 9638186 A1 | 12/1996 |

OTHER PUBLICATIONS

Scher et al, "Effects of oxidized cellulose and microfibrillar collagen on infection," 1982, Surgery, 91(3), pp. 301-304.*
Haiyan Zhou, The Effect of Berberine Chloride on Experimental Colitis in Rats in Vivo an d in Vitgro May 15, 2000, 8 pages, vol. 294, No. 3, Department of Preventive Medicine, of Social Medicine, Medical Research Institute, Tokyo Medical and Dental University, Tokyo, Japan.
Baird et al. (1997) "Non-antibiotic anti-diarrhoeal drugs: factors affect oral bioavailability of berberine and loperamide in intestinal tissue"; Adv. Drug. Deliv. Review; 23:111.
Publication# XP008107429 "Nutrient fodder additive—contains silkworm excrement, coal, yeast, white alkali, vitamin(s) and berberine, etc.", WPI/Thomson, Sep. 23, 1998, RE: Chinese Patent No. 1193471, issued Sep. 23, 1998 to Zhao et al.
Dutta et al. (1972) "Berberine in Toxin Induced Experimental Cholera"; Br. J. Pharm.; 44:153.
Sack et al. (1982) "Berberine Inhibits Intestinal Secretory Response of *Vibrio cholerae* and *Escherichia coli* Enterotoxins"; Infect. Immun.; 35:471.
Guandalini et al. (1987) "Effects of Berberine on Basal and Secretagogue-Modified Ion Transport in the Rabbit Ileum In Vitro"; J. Pediatr. Gastroenterol.; 6:953.
Taylor et al. (1995) "Berberine Inhibition of Electrogenic Ion Transport in Rat Colon"; Br. J. Pharmacol.; 116:2267.
"A Natural Approach to Irritable Bowel Syndrome" (Feb. 24, 2001) <http://web.archive.org/web/*/www.rexdonald.com/constipation/irritablebowelsyndrome.htm> (Retrieved Aug. 17, 2010).
Zhou et al. (2000) "The Effect of Berberine Chloride on Experimental Colitis in Rats In Vivo and In Vitro"; The Journal of Pharmacology and Experimental Therapeutics; 294(3):822-829.
International Search Report (ISR) Dated Oct. 20, 2004, for International Patent Application No. PCT/AU2004/001151 Filed Aug. 26, 2004.
Written Opinion Dated Oct. 20, 2004, for International Patent Application No. PCT/AU2004/001151 Filed Aug. 26, 2004.
International Preliminary Report on Patentability (IPRP) Dated Jan. 1, 2006, for International Patent Application No. PCT/AU2004/001151 Filed Aug. 26, 2004.
Supplementary European Search Report Dated Mar. 23, 2009, for European Patent Application No. 04761188, Filed Aug. 26, 2004.
Office Action Dated Oct. 20, 2010, for Canadian Patent Application No. 2536489.
Baird et al. (1997) "Non-antibiotic anti-diarrhoeal drugs: factors affect oral bioavailability of berberine and Ioperamide in intestinal tissue"; Adv. Drug. Deliv. Review; 23:111.
Chopra et al. (1932) "Pharmacological action of berberine"; Indian J. Med. Res.; 19:1193.
Publication# XP008107429 "Nutrient fodder additive—contains silkworm excrement, coal, yeast, white alkali, vitamin(s) and berberine, etc.", WPI/Thomson, 19980923, RE: Chinese Patent No. 1193471, issued Sep. 23, 1998 to Zhao et al.
Sabir et al. (1977) "Antagonism of cholera toxin by berberine in the gastrointestinal tract of adult rats"; Indian J. Med. Res.; 65:305.
Tai et al. (1981) "Antisecretory effects of berberine in rat ileum"; Am. J. Physiol.; 241:G253.
Tancrède (1992) "Role of human microflora in health and disease"; Eur. J. Clin. Microbiol. Infect. Dis.; 11:1012.
Tang et al. (1992) "In Chinese Drugs of Plant Origin"; pp. 361-371, Springer-Verlag Press: London.
Taylor et al. (1999) "Berberine inhibits ion transport in human colonic epithelia"; Eur. J. Pharmacol.; 368:111.
Yamamoto et al. (1993) "Pharamcological studies on anti-diarrhoeal effects of a preparation containing berberine and gerainii herba"; Nippon Yakurigaku Zasshi; 101:169, English language figures and abstract considered.
Zhang et al. (1991) "Two new 8-oxotetrahydroprotoberberine alkaloids, gusanlung A and B from Acangelisia gusanlung"; Planta Med.; 57:457.
Atarashi et al. (Jan. 21, 2011) "Induction of Colonic Regulatory T Cells by Indigenous *Clostridium* Species"; Science; 331:337-341.
Bartlett (2010) "Clostridium Difficile: Progress and Challenges"; Ann. N.Y. Acad. Sci.; 1213:62-69.
Salamon (Feb. 2, 2011) "New Antibiotic Helps Prevent Recurrence of Dangerous Gut Infection"; Yahoo! News; 3 Pages.
Nano (Jan. 6, 2011) "Antibiotic Shown to Relieve Common Bowel Disorder"; Yahoo! News; 3 Pages.
Wikipedia.org (Retrieved Jan. 6, 2011) "Rifaximin"; http://en.wikipedia.org/wiki/Rifaximin.
Wikipedia.org (Retrieved Feb. 3, 2011) "Fidaxomicin"; http://en.wikipedia.org/wiki/Fidaxomicin.

* cited by examiner

COMPOSITIONS FOR VETERINARY AND MEDICAL APPLICATIONS

CROSS-REFERENCE TO RELATED APPLICATION

This is a continuation application that claims benefit, under 35 USC §120, of co-pending International Application PCT/AU2004/001151, filed on 26 Aug. 2004, designating the United States, which claims foreign priority benefits under 35 USC §119 (a) to Australian Patent Application No. 2003904654, filed 28 Aug. 2003, and Australian Patent Application No. 2003904817 filed 4 Sep. 2003, which applications are incorporated herein by reference.

BACKGROUND TO THE INVENTION

Gastrointestinal ("GI") function disorders are caused by the invasion of pathogens, post treatment of broad-spectrum antibiotics, improper diet, stressful lifestyle and other causative factors. They are very common diseases, with conditions such as Irritable Bowel Syndrome (IBS) presenting in as much as 20% of the adult population in the USA. In Canada, IBS is second only to the common cold as the leading cause of time absent from school and work. So far, there is no effective medicine for the treatment IBS and Inflammatory Bowel Disease (IBD). Desirably, compositions for therapeutic purposes should meet the following criteria:

Non-toxic, safe to use.
Not inhibiting or adversely affecting probiotic bacteria in the gut.
Preferably very poor oral bioavailability (no systemic effects).
Not causing bacterial resistance.
Anti-inflammatory.
Anti-diarrhea, antisecretory.
Anti-motility.
Strengthening immunity.
Neutralizing toxins.

This invention seeks to provide compositions and treatments for GI functional disorders which meet one or more of the above criteria.

In humans, the gastrointestinal (GI) tract with an area of 300-400 m² is the second largest surface connecting the body with the outside world. With consumption of 1~2 kg of food every day, the GI immune system is presented with the threat of ingested poisons and pathogens together with an enormous variety of harmless antigens. The GI tract digests food and absorbs the nutrients that are beneficial to the body, while eliminating components that pose a potential risk to health. A large portion of the body's immune system is located in the GI wall and the mesenteric lymph nodes, called gut-associated lymphoid tissue (GALT) system. GI secretions are rich in antimicrobial factors such as lactoferrin and lysozyme and other factors, like important growth and mucosa healing factors such as epidermal growth factor (EGF). The mucosa of the gut is normally covered by a unique protective layer of mucus and is colonized by microflora, which perform a key function in the regulation of the GALT system.

The mucus serves to a large extent as a matrix for the indigenous protective flora. The intestines contain about 1 kg probiotic bacteria. The roles of these bacteria are to maintain the healthy ecology in the GI tract, synthesizing vitamins, hormones, and other important factors, and to help to break down complex proteins and fiber into smaller molecules that can be absorbed by the mucosal cells.[1]

Pathogenic bacteria in the intestinal tract are an important aspect in the GI functional disorders both as a causative factor and as a symptom. Other disorders can actually cause the GI tract to lose probiotic bacteria and allow pathogenic bacteria growth, eventually, resulting in changes to the intestinal ecology and further exacerbation of the GI functional disorders.

For the treatment of GI functional disorders it is important to restore healthy ecology. This invention relates to the treatment of GI functional disorders and related conditions including IBS and IBD including colitis, Crohn's disease and coeliac disease. The treatment is expected to improve intestinal health and reduce symptoms including constipation, flatulence and diarrhea. It acts as a GI cleanser, strengthening the immune system, inhibiting and removing the pathogenic bacteria, and helping to restore a healthy ecology in the intestinal tract. The resulting healthy digestion system will support the healthy state of the body and healthy weight gain in animals including humans.

Berberine is an isoquinoline quaternary alkaloid derived from a number of species of the barberry plant including *Berberis aristata* and *Coptis chinensis*.[2] Structural analogues of berberine have been isolated from extracts of the Chinese medicinal plant, *Acangelisia gusanlung*.[3] which has been used for over 2000 years in traditional Eastern medicine to treat gastro-enteritis and secretory diarrhea[4] and is also effective in the prevention and the treatment of animal models of diarrhea.[5-7] Berberine possesses antimicrobial[4], anti-motility[8] and anti-secretory properties.[9-11] Thus, several mechanisms may contribute to the therapeutic usefulness of berberine. Berberine has been used as an anti-diarrhea drug at dose range of 100 mg~300 mg t.i.d. in adult (6 mg~18 mg/kg/day) in China.[12] Finally the apparent permeability coefficient (Papp) of berberine across the intestinal tissue was of the order of $10^{-7}$ cm/s[13], typical of the values of poorly absorbed compounds, and reflected by poor bioavailability in vivo. This poor oral bioavailability causing poor systemic absorptions should offer the benefit of safe use of the oral administration of berberine.

Certain saturated lower dialdehydes also possess antibacterial activity toward sulfate-reducing bacteria.[14] Furthermore, alcoholic sporicidal compositions containing similar saturated lower dialdehydes were taught.[15] Also it is known that water-soluble dialdehyde starch can be incorporated into chewing gum compositions as a cariostatic agent[16], a water insoluble dialdehyde polysaccharide being applied in medium at a concentration of at least about 0.1 weight percent to inhibit the bacterial growth.[17] Synthetic polymeric dialdehydes such as poly-(2-propenal, 2-propenoic acid) have been used in the treatment of gastrointestinal diseases. However, since the antimicrobial activities of these compounds are very weak, very high doses for treatment, such as 500~2500 mg/kg body weight/day are required.[18]

After searching and screening it has been found that compositions including compounds of Formula (1) below, (particularly berberine chloride), and compounds of Formula (2) below, (particularly oxidized cellulose), are each useful for the treatment of the GI functional disorders and related conditions as well as for a method of promoting weight gain in animals including humans. One of the most important findings of the invention is the existence of a synergic effect obtained by using combination of the compounds of Formula (1) and compounds of Formula (2) (see Example 4 and Example 8, below). This synergic effect provides the possibility of using lower dosage of the compounds, thereby achieving higher safety and economy.

DISCLOSURE OF THE INVENTION

In one aspect, the present invention relates to a composition including a compound of Formula (1) and/or a polymeric dialdehyde, for the treatment of gastrointestinal (GI) functional disorders and related conditions, including Irritable Bowel Syndrome (IBS); Inflammatory Bowel Disease (IBD), Colitis, Crohn's disease and coeliac disease; and/or for promoting weight gain in animals, where Formula (1) comprises:

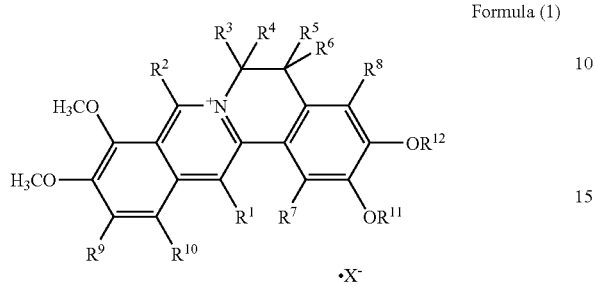

Formula (1)

·X⁻ where $R^1, R^2, R^7, R^8, R^9$, and $R^{10}$ may be the same or different and are selected from H, $CH_3$, OH, $OCH_3$, $C_2H_5$, $OC_2H_5OCH_2Ph$, $OCH_2PhNO_2$, F or Cl;
$R^3, R^4, R^5, R^6$ may be the same or different and are selected from H, $CH_3$, $OCH_3$, $C_2H_5$, $OC_2H_5OCH_2Ph$, $OCH_2PhNO_2$, F or Cl, or
$R^5$ and $R^6$ are the same or different and are selected from H, $CH_3$, $OCH_3$, $C_2H_5$, $OC_2H_5OCH_2Ph$, $OCH_2PhNO_2$, F or Cl and $R^3$ and $R^4$ together are =O, or
$R^4$ and $R^6$ are the same or different and are selected from H, $CH_3$, $OCH_3$, $C_2H_5$, $OC_2H_5OCH_2Ph$, $OCH_2PhNO_2$, F or Cl and $R^3$ and $R^5$ together form a double bond or are =O, or
$R^3$ and $R^4$, are the same or different and are selected from H, $CH_3$, $OCH_3$, $C_2H_5$, $OC_2H_5OCH_2Ph$, $OCH_2PhNO_2$, F or Cl and $R^5$ and $R^6$ together are =O;
$R^{11}$ and $R^{12}$ together form =$CH_2$, or $R^{11}$ and $R^{12}$ may be the same or different and are independently selected from the group consisting of H, $CH_3$, $CH_2CH_3$ and $CH_2CH_2CH_3$; and $X^-$ is selected from the group consisting of Cl, Br, $SO_4$, I and $R^{13}COO$, where $R^{13}$ is $CH_3$ or poly acids.
Preferably, $R^1, R^2, R^3, R^4, R^5, R^6, R^7, R^8, R^9$ and $R^{10}$, are hydrogen, $R^{11}$ and $R^{12}$ together form $H_2C=$ and $X^-$ is Cl so that Formula (1) is berberine chloride.
The polymeric dialdehyde may be chosen from a wide range of suitable compounds. For example poly-(2-propenal, 2-propenoic acid) may be combined with a compound of Formula (1) to form the compositions of this invention. Preferably, the polymeric aldehyde is a dialdehyde polysaccharide. Particularly preferred dialdehyde polysaccharides have a formula in accordance with Formula (2):

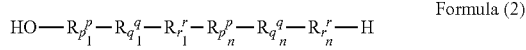

Formula (2)

wherein each of the monomers $R^p$ and $R^r$, are independently selected from the group consisting of:

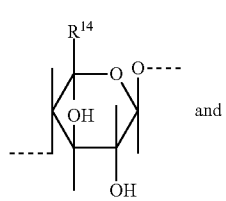

(A)

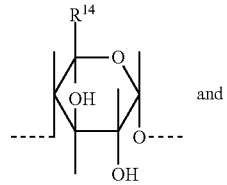

(B)

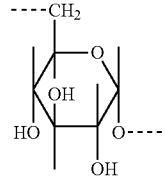

(C)

and each monomer $R^q$ is independently selected from the group consisting of:

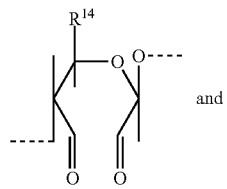

(D)

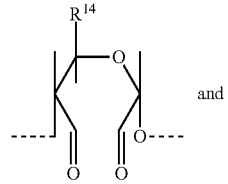

(E)

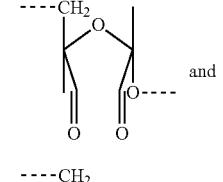

(F)

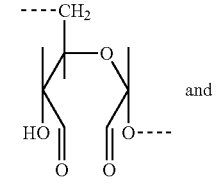

(G)

wherein each $R^{14}$ may be the same or different and is independently selected from the group consisting of $CH_2OH$, COOH, $CH_2OCH_2COOH$ and $CH_2OR^{15}$, where $R^{15}$ is selected from the group consisting of $CH_2C_6H_4COOH$, $C_6H_4COOH$ and $CH_2(CH_2)_yCOOH$ where y=1 to 20;
wherein $p_i \ldots p_n$ may be the same or different and are each independently selected from the range 0 to n; $q_1 \ldots q_n$ may be the same or different and are each independently selected from the range 1 to m, preferably from the range 2 to m; $r_1 \ldots r_n$ may be the same or different and are each independently selected from the range of 0 to n, n is an integer greater than 0 and m is an integer greater than 1; and wherein $$\frac{q_1 + \cdots + q_n}{p_1 + \cdots + p_n + q_1 + \cdots + q_n + r_1 + \cdots + r_n} \times 100\% \geq 30\%$$

In one preferred embodiment, each $R^p$ and $R^r$ are (A) and $R^q$ is (D), so that the polymeric dialdehyde is oxidised cellu lose. In this case, it is also preferred that $R^{14}$ is $CH_2OH$ or $CH_2OCH_2COOH$.

In another preferred embodiment, each $R^p$ and $R^r$ are (B) and $R^q$ is (E), so that the polymeric dialdehyde is oxidised starch or dextrin.

In another preferred embodiment, each $R^p$ and $R^r$ are (C) and each $R^q$ is (F) or (G) so that the polymeric dialdehyde is oxidised dextran.

In each case, it is preferred that:

$$\frac{q_1 + \cdots + q_n}{p_1 + \cdots + p_n + q_1 + \cdots q_n + r_1 + \cdots + r_n} \times 100\% \geq 40\%$$

and particularly preferred that:

$$40\% \leq \frac{q_1 + \cdots + q_n}{p_1 + \cdots + p_n + q_1 + \cdots + q_n + r_1 + \cdots + r_n} \times 100\% \leq 60\%$$

that is, the oxidised cellulose, starch, dextrin or dextran is from 40% to 60% oxidised.

The compounds of Formula (2) preferably have a molecular weight of from 1,000 to 1,000,000. More preferably, they have a molecular weight of from 10,000 to 750,000. Where the compounds of Formula (2) are water-insoluble, they preferably have a particle size of from 5μ to 100μ, more preferably from 5μ to 30μ. For example, the diameter of microcrystalline oxidized cellulose is about 20μ.

Generally, the oxidized rate of the Formula (2) is from 30~100%, preferably 40~100%, more preferably 40~60%. It was found that the compounds of the Formula (2) were non-toxic by oral administration. In particular, the oxidized celluloses are relatively stable in the GI tract. Their high molecular weights prevent them being absorbed by gut. Their polydialdehyde functional groups interact and neutralize toxins. The compounds of the Formula (2) possess an anti-constipation effect. The compounds also promote ulcer healing. The compounds do not adversely affect the growth of probiotic bacteria in gut.

Animals to which the composition may be administered include: primates including humans, birds including poultry, ungulates including cattle, sheep, horses, cervidae and swine, fish including crustaceans and molluscs, reptiles, rodents, canines and felines.

In another embodiment, the invention comprises using compounds of Formula (1) and compounds of Formula (2) in the manufacture of a medicament for the treatment of GI functional disorders and related conditions including Irritable Bowel Syndrome (IBS); Inflammatory Bowel Disease (IBD) including Colitis, Crohn's disease and coeliac disease; and for promoting weight gain in animals including humans.

In another embodiment, the invention comprises a method of treating gastrointestinal disorders including Irritable Bowel Syndrome (IBS); Inflammatory Bowel Disease (IBD), colitis, Crohn's disease and coeliac disease, including administering to an animal, including a human, suffering from a gastrointestinal disorder, effective amounts of a compound of Formula (1) and/or polymeric dialdehyde. Preferably, the method of treatment comprises administering effective amounts of a compound of Formula (1) and polymeric dialdehyde in conjunction. In different embodiments of the invention treatment may comprise administering the compound of Formula (1) and the polymeric dialdehyde sequentially or simultaneously. In a preferred embodiment the compound of Formula (1) is combined with the polymeric dialdehyde to form a composition which is then administered. Preferably the polymeric dialdehyde is a compound of Formula (2), more preferably oxidised cellulose, especially oxidised cellulose having an oxidation level of from 40% to 60%.

The required dose of the composition containing Formula (1) and a polymeric dialdehyde is generally less than 50% of those separately using individual components. For example, the dose of berberine is 6 mg~18 mg/kg/day for adult. The use of 40% oxidized cellulose is 250 mg~750 mg/kg/day. However, when using combination of berberine and 40% oxidized cellulose the required dose is berberine 0.5 mg~6 mg/kg/day plus 40% oxidized cellulose 5 mg~200 mg/kg/day. Preferably, in humans, a dose of berberine 0.5 mg~3 mg/kg/day plus 40% oxidized cellulose 5 mg~80 mg/kg/day is used.

In addition, effective amounts of a compound of Formula (1) and polymeric dialdehyde may be administered in conjunction to promote weight gain in animals, including humans. In this context the compounds may be administered as feed additives. Accordingly, the invention includes modified foods containing from 0.1 to 50 ppm of a compound of Formula (1) and from 1 to 400 ppm of a polymeric dialdehyde. Preferably, the modified food contains from 2 to 10 ppm of a compound of Formula (1) and from 10 to 200 ppm of a compound of Formula (2); more preferably Formula (1) is berberine chloride and Formula (2) is oxidized cellulose.

It is envisioned that the compound of Formula (1) and the polymeric dialdehyde may be provided separately, rather than as a composition. The present invention also comprises a kit including a quantity of a compound of Formula (1) and a quantity of a polymeric dialdehyde for the treatment of gastrointestinal (GI) functional disorders and related conditions including Irritable Bowel Syndrome (IBS); Inflammatory Bowel Disease (IBD) including colitis, Crohn's disease and coeliac disease; and for promotion of weight gain in animals including humans. Preferably the weight ratio of the quantity of compound of Formula (1) to the quantity of polymeric dialdehyde ranges from 1:1 to 1:100, more preferably from 1:10 to 1:40.

It has also been found that berberine selectively inhibits pathogenic bacteria such as *Staphylococcus aureus*, *Streptococcus* Group B, *Vibrio cholerae*, *Clostridium perfringens*, *Candida albicans*, but does not inhibit beneficial bacteria (probiotics) such as *Lactobacillus plantarum* at <500 □g/ml (see Table 1).

TABLE 1

Antimicrobial Activities of berberine, oxidized cellulose and Erythromycin

| | Minimum Inhibitory Concentration (□g/ml) | | |
| --- | --- | --- | --- |
| Microorganism | Berberine | Oxidized cellulose | Erythromycin |
| *Staph. Aureus* ATCC 29213 | 125 | >1,000 | <0.625 |
| *Strep.* Group B MCR1 27 | 62.5 | >1,000 | <0.625 |
| *E. coli* HS | >500 | >1,000 | >10 |
| *V. cholerae* 6239 | 125 | >1,000 | >10 |
| *C. albicans* ATCC 14053 | 62.5 | >1,000 | >10 |
| *Cl. perfringens* ATCC 1124 | 125 | >1,000 | 1.25 |
| *L. plantarum* | 500 | >1,000 | <0.625 |

Pathogenic bacteria like *Escherichia Coli* lost their filaments and were unable to attach on the wall of intestine after being treated with berberine at 5 □g/ml, which is a much lower concentration than MIC (Minimum Inhibition Concentration). However, at this concentration, berberine did not affect probiotic bacteria such as *Lactobacilli*. This specific property of berberine offers an important aspect as a GI tract cleanser, since it can selectively remove pathogenic bacteria from the gut without affecting the inhabitations of the probiotic bacteria in GI tract, and without exerting excessive drug pressure on the bacteria, which may lead to drug resistance.

The currently available broad spectrum antibiotics indiscriminately inhibit both pathogenic and probiotic bacteria in gut. Antibiotic treatment often causes GI function disorders. Animals and plants have coexisted with microbes throughout their evolution, sometimes to their mutual benefit, often in an antagonistic relationship. Berberines are an ancient and pervasive component of the innate defense mechanisms; they have developed to control the natural flora and combat pathogens. They do not target specific molecular receptors on the microbial surface. This characteristic may avoid the problem of inducing bacterial resistance occurred to most antibiotics. It was also found that berberine could induce the interleukine-12 (IL-12) (pro-antiinfectious) and inhibit the production of IL-8 (pro-inflammatory). This antiinflammatory property strengthening the host immunity is also very useful for the treatment of IBD and IBS.

In addition to use of the compounds of Formula (1), it has been found that compounds of Formula (2) not only possess antibacterial activity, but are also able to neutralize toxins and act as an antioxidant.

Accordingly, the research leading to the present invention also discloses the invention of treating Irritable Bowel Syndrome, Inflammatory Bowel Disorder, Colitis, Crohn's disease and ceoliac disease including administering an effective amount of a compound of Formula (1) or of Formula (2) to an animal, including a human, in need thereof.

The invention also provides a method of promoting weight gain in animals including humans including administering an effective amount of a compound of Formula (1) and/or Formula (2).

Hereinafter, GI tract cleansing compositions that include compounds of Formula (1) and compounds of Formula (2), and/or the pharmaceutically acceptable derivatives thereof may be referred to as GILAX cleaners. The amount of GILAX-cleanser required for use in treatment will vary with the nature of the condition being treated and the age condition of the animal including human patients, and will ultimately be at the discretion of the attendant veterinarian or physician.

In general, a GILAX-cleanser comprises the compounds of Formula (1) and the compounds of Formula (2) at a weight ratio of 1:1~100, preferably at a weight ratio of 1:10~40. For example, for humans, the dose of GILAX-cleansers (for instance, berberine chloride and oxidized cellulose at a weight ratio of 1:10) may be 275~1650 mg/day orally. The dose taken is according to the GI functional disorder condition. It is recommended for an adult to take 550 mg once daily for IBS or post antibiotic GI functional disorder, 275 mg×2 daily for IBD, 550 mg×4 daily for acute diarrhea or other severe conditions.

In animal farming, such as the poultry industry, GILAX-cleansers may be used as food additives to promote growth. The composition is preferably 1~20 ppm of berberine plus 10~400 ppm of oxidized cellulose; more preferably, 5 ppm of berberine plus 50 ppm of oxidized cellulose.

In swine industry, GILAX-cleansers can be used to protect piglets from diarrhea. A composition including 0.5 mg~6 mg of Formula (1) (berberine)/kg/day and 50 mg~200 mg of Formula (2) (oxidized cellulose)/kg/day may be used.

A GILAX-cleanser composition is preferably formed by combining the compounds of Formula (1) and the compounds of Formula (2) with one or more other ingredients, for example: vitamins, antibiotics, antiseptic agents, surfactants, antidiarrheal agents, anti-constipation agents, enzymes, (especially digestive enzymes), probiotic bacteria, herbs, vaccines, ulcer healing agents (e.g. gibberellins, glucans).

In accordance with the invention, a pharmaceutical formulation including the GILAX-cleansers or pharmaceutically acceptable derivatives thereof may also contain one or more pharmaceutically acceptable carriers and, optionally, other therapeutic and/or prophylactic ingredients. The carriers must be acceptable in the sense of being compatible with the other ingredients of the formulation and not deleterious to the recipient thereof.

Pharmaceutical formulations may be in any form suitable for administration to the gastrointestinal tract, including those suitable for oral, and rectal administration. While it is possible that for use in therapy, the GILAX-cleansers may be administered as the raw chemical(s), it is preferable to present the active ingredient(s) as a pharmaceutical formulation. The formulation may, where appropriate, be conveniently presented in discrete dosage units and may be prepared by any of the methods known in the art of pharmacy. Preferably, the methods include the step of bringing into association the active compound(s) with liquid carriers or finely divided solid carriers or both and then, if necessary, shaping the product into the desired formulations.

Pharmaceutical formulations suitable for oral administration may be presented as discrete units such as capsules, cachets, or tablets each containing a predetermined amount of the active ingredient(s); as a powder or granules; a solution, a suspension or as an emulsion. The active ingredient(s) may also be presented as a bolus, electuary or paste. Tablets and capsules for oral administration may contain conventional excipients such as binding agents; fillers, lubricants, disintegrants, or wetting agents. The tablets may be coated according to methods known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

For administration to a gastrointestinal ulcer such as peptic ulcer, the compounds of GILAX-cleanser or pharmaceutically acceptable derivatives thereof may be administered by any of the methods and formulations employed in the art of administration to the gastrointestinal tract.

Where desired, formulations adapted to give sustained release of the active ingredient may be employed.

The compounds of the GILAX-cleansers may also be used in combination with other therapeutic agents, for example, anti-infection agents, such as antibiotics, or ulcer healing agents such as gibberellins, glucans, growth factors (EGF), and/or probiotic bacteria such as *Lactobacillus plantarum*.

The combinations mentioned above may conveniently be presented for use in the form of a pharmaceutical formulation and thus such formulations including a combination of compounds of Formula (1) and of Formula (2) as defined above, together with a pharmaceutically acceptable carrier therefore comprise a further aspect of the invention.

When the compounds of GILAX-cleansers are used with a second therapeutic agent active in the treatment of GI functional disorders and related conditions, the dose of each compound may either be the same as or differ from that employed when each compound is used alone. Appropriate doses will be readily appreciated by those skilled in the art.

The compounds of GILAX-cleansers and their pharmaceutically acceptable derivatives may be prepared by any methods known in the art for the preparation of compounds of analogous structure.

EXAMPLES

The invention will now be discussed with reference to examples. The examples are by way of illustration only and should not be construed as any limitation on the scope of the invention.

Example 1

Preparation of a Compound of Formula (1), Berberine Chloride

The root and bark of berberines vulgaris (1.5 kg, grounded) was refluxed with ethanol (10 L×2). The ethanol extracts was filtered and evaporated under reduced pressure to afford a brownish oil. This residue was dissolved in a warm 0.1M HCl solution (10 L×2), filtered, and the filtrate was vacuum evaporated to about 1 L, then stirred at room temperature overnight. The yellow precipitates were collected and washed with cold water, then redissolved in boiling water (10 L×2), cooled to room temperature to afford berberine chloride (44.5 g) as yellow crystalline powder after filtration, washing with water, and air-drying. Analysis of the crystals using NMR produced the following results:

$^1$H-nmr (CD$_3$OD)×(ppm)
3.16 (t, 2H), 4.02 (s, 3H), 4.15 (s, 3H), 4.88 (t, 2H), 6.12 (s, 2H), 7.03 (s, 1H), 7.74 (s, 1H), 7.95 (d, AB, 1H), 8.15 (d, AB, 1H), 8.89 (s, 1H), 9.83 (s, 1H).

Example 2

Preparation of a Compound of Formula (2), 40% Oxidized Cellulose

To a stirring solution of periodic acid (140.7 g, 0.6175 mole) in water (1.08 L) at pH<0.5 was added in portions microcrystalline cellulose (particle size of ~20 in diameter) (250 g, 1.54 mole) at <30° C. over a period of 2 hours. The whole mixture was stirred at 30~32° C. for 4 hours, then at room temperature for 16 hours. To this resulting reaction mixture was added a 5% sodium hydroxide solution (~480 ml) to adjust the solution pH to 5-6. The suspension was filtered; the solid was washed with water (2 L×4) until the filtrate on KI-starch test paper showed the absence of the oxidant. The solid was then washed with acetone (0.5 L) and air dried to afford 40% oxidized cellulose as a white powder (215 g, 87%).

Example 3

Preparation of a Compound of Formula (2) 40% Oxidized Water Soluble Cellulose

To a stirring solution of carboxymethyl cellulose (MW 250,000, DS=0.7) (1 g, 6.17 mmole) in water (25 ml) in an ice-bath, a solution of sodium periodate (532.5 mg, 2.48 mmole) in water was added dropwise over a period of 2 hours. The reaction mixture was stirred at 5-10° C. for 16 hours, then dialysed against water in a dialysis tube (the cut-off MW~10,000) for 48 hours. The solution was then freeze dried to afford 40% oxidized water soluble cellulose as a white powder (813 mg, 81.4%).

Example 4

Pilot Chicken Experiment

Male day old chickens (white Leghorn □ New Hampshire) were fed Barastoc chicken crumbles, which contain zinc bacitracin and D.O.T. (3,5-dinitro-ortho-tuluamide) and antioxidants ethoxyquin and B.H.T. for 13 days. On day 14, they were randomly divided into six groups of five chickens each, with the average weight of chickens from each group varying from 121.4 g to 124.2 g (2.3% variance between all the groups). The chickens were then fed with same basic growers pellets, which did not contain any antibiotics but do contain D.O.T., with different food additives shown as follows:
Group A: feed additive is 50 ppm berberine chloride.
Group B: feed additive is 10 ppm berberine chloride.
Group C: feed additive is 200 ppm 40% oxidized cellulose.
Group D: feed additive is 100 ppm 40% oxidized cellulose.
Group E: feed additive is 5 ppm berberine chloride+50 ppm 40% oxidized cellulose.
Control: no feed additive.

The chickens were fed for another 23 days. Observation was carried out on the feed intake, weight gains, colour of combs (a red coloured comb indicates a healthy state of the bird), and mortality. There were no fatalities in the experiment. There were no significant differences in the amount of feed intakes among the groups. The statistical analysis was performed two-tailed at a significance level of p=0.05. The results were shown in Table 2.

TABLE 2

Synergic effect of the composition of the compound of Formula (1) (berberine chloride) and the compound of Formula (2) (40% oxidized cellulose) on chicken growth

| Experimental Group | Red Combs (Number of red comb/total number of chickens | | | | | | | Growth rate compared to that of the control on day 36 |
| --- | --- | --- | --- | --- | --- | --- | --- | --- |
| | Day 14 | Day 17 | Day 21 | Day 24 | Day 26 | Day 32 | Day 36 | |
| A | 0/5 | 1/5 | 1/5 | 3/5 | 3/5 | 4/5 | 4/5 | 106.36% (p = 0.05) |
| B | 0/5 | 0/5 | 2/5 | 2/5 | 3/5 | 4/5 | 5/5 | 101.79% |
| C | 0/5 | 1/5 | 1/5 | 1/5 | 4/5 | 4/5 | 5/5 | 101.74% |
| D | 0/5 | 0/5 | 0/5 | 0/5 | 1/5 | 2/5 | 3/5 | 99.82% |
| E | 0/5 | 1/5 | 1/5 | 1/5 | 2/5 | 5/5 | 5/5 | 108.11% (p = 0.05) |
| Control | 0/5 | 0/5 | 0/5 | 0/5 | 0/5 | 1/5 | 1/5 | 100.00% |

There was no residue of either berberine or oxidized cellulose found in the meat of chickens.

Example 4, demonstrates the synergic effect of the invention. From the results, it is clear that the composition of 5 ppm berberine plus 50 ppm oxidized cellulose gave the best growth promotion compared to 20 ppm berberine or 10 ppm berberine or 200 ppm oxidized cellulose, or 100 ppm oxidized cellulose alone. This synergic effect provides the possibility of using lower dosages of the compounds, thereby achieving higher safety and economy.

Example 5

Preparation of GILAX-Cleanser a) Berberine chloride 50 mg mixed with 40% oxidized cellulose 500 mg was packed in a capsule for oral administration for adult for the treatment of IBS or post antibiotic GI functional disorder or diarrhea.
b) Berberine chloride 25 mg mixed with 40% oxidized cellulose 250 mg was packed in a capsule for oral administration for the treatment of IBD.

Example 6

Combination of GILAX-Cleanser with Probiotic Bacteria for the Treatment of IBS and IBD GILAX-cleanser from example 5 may be used sequentially or simultaneously with the preparation of probiotic bacteria. Probiotic bacteria capsule or tablet, protected from air, contains $0.5 \sim 1 \times 10^{10}$ CFU/capsule or tablet. Its composition is shown as follows:

| | |
|---|---|
| *Bifidobacterium bifidum* | 30% |
| *Bifidobacterium longum* | 20% |
| *Lactobacillus plantarum* | 10% |
| *Lactobacillus bulgaricus* | 10% |
| *Lactobacillus salivarius* | 10% |
| *Lactobacillus acidophilus* | 20% |

Example 7

Compound of Formula (2), 40% Oxidized Cellulose as Food Additive to Promote Chicken Growth The chicken experiment was set up substantially as described in example 4, but with 6 chickens in each of the experimental and control groups. However, the feed additive was 1,000 ppm of 40% oxidized cellulose. The growth rate of the experimental group of six chickens was 3.86% (p=0.05) higher than the six chickens in the control group.

Example 8

Synergic Effect of the Compound of Formula (1) and the Compound of Formula (2) on the Treatment of IBD on Mouse Model hFUT1 mouse model of colitis was used. It provides insights into the pathogenesis of Inflammatory Bowel Disease (IBD). These mice do not develop disease in a germ free environment. Immune dysfunction contributing to IBD in humans includes abnormal T cell reactivity and a loss of tolerance to gut bacteria. The compositions of Formula (1) and Formula (2) were given orally to mice to see the effectiveness on the altering the gut flora and lessening the severity of the colitis. The positive results indicated the compositions of Formula and Formula (2) may have a therapeutic role in human IBD.

A total five groups with ten mice per group were used as follows.
1) Control (without treatment).
2) Treated with compound of the Formula (1) (berberine chloride), 13.5 mg/kg/day (o.s.).
3) Treated with compound of the Formula (2) (40% oxidized cellulose), 114 mg/kg/day (o.s.).
4) Treated with composition of the Formula (1) (berberine chloride) (6.7 mg/kg/day) and the Formula (2) (40% oxidized cellulose) (57 mg/kg/day) (o.s.).
5) Treated with composition of the Formula (1) (berberine chloride) (13.5 mg/kg/day) and the Formula (2) (114 mg/kg/day) (o.s.).

The results are shown in Table 3.

TABLE 3

Synergic effect of the composition of the compound of Formula (1) (berberine chloride) and the compound of Formula (2) (40% oxidized cellulose) on IBD in mice

| Group No | Survival rate after 56 days treatment |
|---|---|
| 1 | 3/10 |
| 2 | 5/10 |
| 3 | 5/10 |
| 4 | 9/10 |
| 5 | 9/10 |

Example 9

Tolerance Dose Testing of the Compound of Formula (1) (Berberine Chloride) and the Compound of Formula (2) (40% Oxidized Cellulose) on Balb-C Mice male and 30 femal Balb-C mice were divided into groups of 10. 10 male and 10 female mice were in each of three groups as follows;
1) Control (without compound).
2) Oral administration (gavaged) with berberine chloride 250 mg/kg/day for 14 consecutive days.
3) Oral administration (gavaged) with 40% oxidized cellulose 1330 mg/kg/day for 14 consecutive days.

All mice in the experiment survived and they were all healthy and no significant difference between the groups.

The histological observation on the tissue slides (liver, kidney, lung, intestine) from the tested mice showed no abnormality.

Example 10

Evaluation of GILAX as Feed Additive for Pig Health after Weaning

Most pig farms run in a traditional continuous flow system with some co-mingling of weans, limited age group separation and routine pig flow between site areas. These factors can lead to incidents of diarrhea after weaning. It is aimed to see if GILAX cleanser could provide effective health protection on weans.

A randomized block design assigned sex-matched individual pens per treatment group at weaning. Each pen held 15 piglets (21 days old) three pens were used.

1) Positive control. The piglets received in-feed amoxicillin at 50 mg/kg/day for 21 days.
2) Negative control. The piglets received no medicated feed and water for 21 days.
3) GILAX cleanser treatment. The piglets received in feed GILAX cleanser (5 mg/kg/day berberine chloride+50 mg/kg/day 40% oxidized cellulose) for 21 days.

Any sick piglets noted during the study were dosed with injectable amoxicillin (2 g/day×2). In this study the piglets in group 1 (Amoxicillin) and group3 (GILAX) were all healthy, no injectable amoxicillin was needed. Two piglets in group 2 (negative control) were sick and these were injected with antibiotic.

FOOTNOTES

[1] Tancrède C. Role of human microflora in health and disease. Eur. J. Clin. Microbiol. Infect. Dis. 11:1012 (1992).
[2] Chopra, R. N., et al., Pharmacological action of berberine. Indian J. Med. Res. 19, 1193-1203 (1932).
[3] Zhang, M. F. et al., Two new 8-oxotetrahydroprotoberberine alkaloids, gusanlung A and B from *Acangelisia gusanlung*. Planta Med. 57, 457~459 (1991).
[4] Tang, W. et al., In Chinese Drugs of Plant Origin. pp 361-371 (1992), Springer-Verlag Press: London.
[5] Dutta, N. K. et al., Berberine in toxin induced experimental cholera. Br. J. Pharm. 44, 153-159 (1972).
[6] Sabir, M. et al., Antagonism of cholera toxin by berberine in the gastrointestinal tract of adult rats. Indian J. Med. Res. 65, 305~313 (1977).
[7] Sack, R. B. et al., Berberine inhibits intestinal secretory response of *Vibrio cholerae* and *Escherichia coli* enterotoxins. Infect. Immun. 35, 471~475 (1982).
[8] Yamamoto, K. et al., Pharmacological studies on antidiarrheal effects of a preparation containing berberine and *gerainii herba*. Nippon Yakurigaku Zasshi, 101, 169~175 (1993).
[9] Tai, Y. H. et al., Antisecretory effects of berberine in rat ileum. Am. J. Physiol. 241, G253~G258 (1981).
[10] Guandalini, S. et al., Effects of berberine on basal and secretagogue-modified ion transport in the rabbit ileum in vitro. J. Pediatr. Gastroenterol. 6, 953~960 (1987).
[11] Taylor, C. T. et al., Berberine inhibition of electrogenic ion transport in rat colon. Br. J. Pharmacol. 116, 2267~2672 (1995). Berberine inhibits ion transport in human colonic epithelia. Eur. J. Pharmacol 0.368, 111~118 (1999).
[12] Chinese Pharmacopoeia Part II p. 437~439 5th Edition (1990).
[13] Baird A. W et al., Non-antibiotic anti-diarrheal drugs: factors affect oral bioavailability of berberine and loperamide in intestinal tissue. Adv. Drug Deliv. Review 23, 111~120 (1997).
[14] U.S. Pat. No. 2,801,216.
[15] U.S. Pat. No. 3,016,328.
[16] U.S. Pat. No. 3,679,792.
[17] U.S. Pat. No. 4,034,084.
[18] a) U.S. Pat. No. 6,410,040.
b) PCT/AU96/00328.

What is claimed is:

1. A composition comprising a synergistically effective amount of a compound of Formula (1) and a dialdehyde polysaccharide for the treatment of gastrointestinal (GI) functional disorders or related conditions or for promoting weight gain in animals, where Formula (1) consists of:

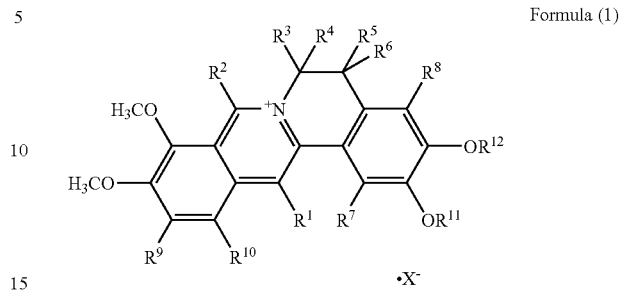

Formula (1)

where $R^1$, $R^2$, $R^3$, $R^4$, $R^5$, $R^6$, $R^7$, $R^8$, $R^9$, and $R^{10}$ are hydrogen and $R^{11}$ and $R^{12}$ together form $=CH_2$; and
X is selected from the group consisting of Cl, Br, $SO_4$, I and $R^{13}COO$, where $R^{13}$ is $CH_3$ or poly acids.

2. A composition according to claim 1 wherein the GI functional disorders or related conditions are selected from the group consisting of Irritable Bowel Syndrome (IBS); Inflammatory Bowel Disease (IBD), Colitis, Crohn's disease and coeliac disease.

3. A composition according to claim 1 wherein the animals are selected from the group consisting of humans and other primates, birds, ungulates, sheep, cervidae and swine, fish, crustaceans, molluscs, reptiles, rodents, canines and felines.

4. A composition according to claim 1 for promoting weight gain in humans, birds, ungulates, fish, reptiles, rodents, canines or felines.

5. A composition according to claim 1 wherein $R^1$, $R^2$, $R^3$, $R^4$, $R^5$, $R^6$, $R^7$, $R^8$, $R^9$ and $R^{10}$ are hydrogen, $R^{11}$ and $R^{12}$ together form $=CH_2$ and $X^-$ is Cl so that the compound of Formula (1) is berberine chloride.

6. A composition comprising a synergistically effective amount of a compound of Formula (1) and a polymeric dialdehyde wherein the polymeric dialdehyde is a dialdehyde polysaccharide of Formula (2), wherein Formula (1) consists of:

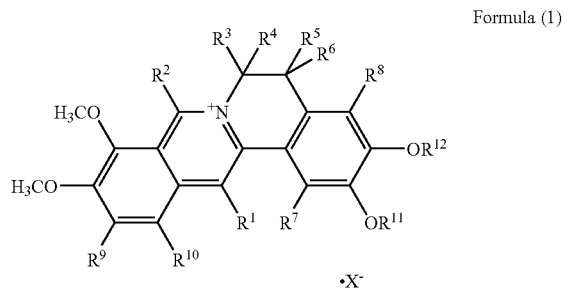

Formula (1)

where $R^1$, $R^2$, $R^3$, $R^4$, $R^5$, $R^6$, $R^7$, $R^8$, $R^9$, and $R^{10}$ are hydrogen and $R^{11}$ and $R^{12}$ together form $=CH_2$; and
X is selected from the group consisting of Cl, Br, $SO_4$, I and $R^{13}COO$, where $R^{13}$ is $CH_3$ or poly acids;
and where Formula (2) consists of:

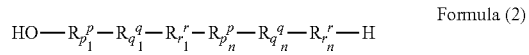

Formula (2)

wherein each of the monomers $R^p$ and $R^r$, are independently selected from the group consisting of:

(A)
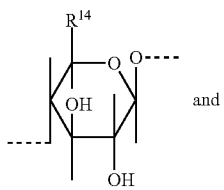
and (B)
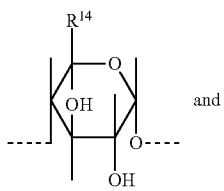
and (C)
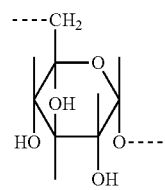

and each monomer $R^q$ is independently selected from the group consisting of:

(D)
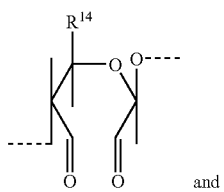
and (E)
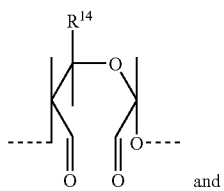
and (F)
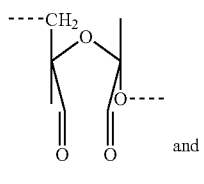
and (G)
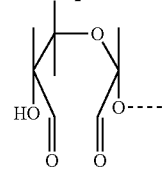

wherein each $R^{14}$ may be the same or different and is independently selected from the group consisting of $CH_2OH$, $COOH$, $CH_2OCH_2COOH$ and $CH_2OR^{15}$, where $R^{15}$ is selected from the group consisting of $CH_2C_6H_4COOH$, $C_6H_4COOH$ and $CH_2(CH_2)_yCOOH$ where y=1 to 20;

wherein $p_1 \ldots p_n$ may be the same or different and are each independently selected from the range 0 to n; $q_1 \ldots q_n$ may be the same or different and are each independently selected from the range 1 to m; $r_1 \ldots r_n$ may be the same or different and are each independently selected from the range of 0 to n, n is an integer greater than 0 and m is an integer greater than 1; and wherein $$\frac{q_1 + \cdots + q_n}{p_1 + \cdots + p_n + q_1 + \cdots + q_n + r_1 + \cdots + r_n} \times 100\% \geq 30\%.$$

7. A composition according to claim 6 wherein each $R^p$ and $R^r$ are (A) and $R^q$ is (D), so that the dialdehyde polysaccharide is oxidised cellulose.

8. A composition according to claim 7 wherein Formula (1) is berberine chloride and wherein the oxidised cellulose is 30 to 100% oxidised monomer.

9. A composition according to claim 8 wherein the oxidised cellulose comprises from 40 to 60% oxidised monomer.

10. A composition according to claim 7 wherein $R^{14}$ is $CH_2OH$ or $CH_2OCH_2COOH$.

11. A composition according to claim 6 wherein each $R^p$ and $R^r$ are (B) and $R^q$ is (E), so that the dialdehyde polysaccharide is oxidised starch or dextrin.

12. A composition according to claim 6 wherein each $R^p$ and $R^r$ are (C) and $R^q$ is (F) and/or (G) so that the dialdehyde polysaccharide is oxidised dextran.

13. A composition according to claim 6, wherein:

$$\frac{q_1 + \cdots + q_n}{p_1 + \cdots + p_n + q_1 + \cdots + q_n + r_1 + \cdots + r_n} \times 100\% \geq 40\%.$$

14. A composition according to claim 6, wherein:

$$40\% \leq \frac{q_1 + \cdots + q_n}{p_1 + \cdots + p_n + q_1 + \cdots + q_n + r_1 + \cdots + r_n} \times 100\% \leq 60\%.$$

15. A composition according to claim 6 wherein the compound of Formula (2) has a molecular weight of from 1,000 to 1,000,000 Daltons.

16. A composition according to claim 15 wherein the compound of Formula (2) has a molecular weight of from 10,000 to 750,000 Daltons.

17. A composition according to claim 6 wherein the compound of Formula (2) is water-insoluble and has a particle size of from 5μ to 100μ.

18. A composition according to claim 17 wherein the compound of Formula (2) has a particle size of from 5μ to 30μ.

19. A composition according to claim 6, where the weight ratio of Formula (1) to Formula (2) ranges from 1:1 to 1:100.

20. A composition according to claim 19 wherein the weight ratio of Formula (1) to Formula (2) ranges from 1:10 to 1:40.

21. A composition including a compound of Formula (1) and a dialdehyde polysaccharide for the treatment of gas trointestinal (GI) functional disorders or related conditions or for promoting weight gain in animals, where Formula (1) is:

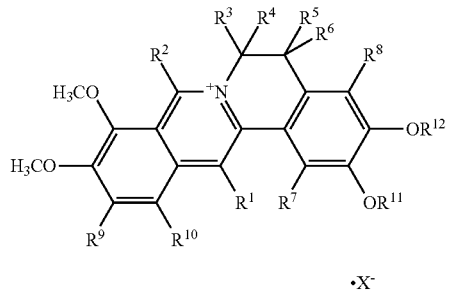

Formula (1)

·X⁻ where $R^1, R^2, R^3, R^4, R^5, R^6, R^7, R^8, R^9$, and $R^{10}$ are hydrogen and $R^{11}$ and $R^{12}$ together form $=CH_2$; and X is selected from the group consisting of Cl, Br, $SO_4$, I and R13COO, where $R^{13}$ is CH3 or poly acids and wherein the compound of Formula (1) is present at a concentration that provides a dosage of less than about 6 mg/kg/day and the dialdehyde polysaccharide is present at a concentration that provides a dosage of less than about 250 mg/kg/day.

22. The composition of claim 21 wherein the compound of Formula (1) is present at a concentration that provides a dosage of less between about 0.5 mg-6 mg/kg/day and the dialdehyde polysaccharide is present at a concentration that provides a dosage of about 5 mg-200 mg/kg/day.

23. A composition including a compound of Formula (1) and a dialdehyde polysaccharide for the treatment of gastrointestinal (GI) functional disorders or related conditions or for promoting weight gain in animals, where Formula (1) is:

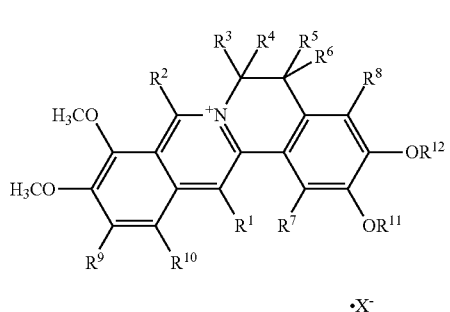

Formula (1)

·X⁻ where $R^1, R^2, R^3, R^4, R^5, R^6, R^7, R^8, R^9$, and $R^{10}$ are hydrogen and $R^{11}$ and $R^{12}$ together form $=CH_2$; and X is selected from the group consisting of Cl, Br, SO4, I and R13COO, where R13 is CH3 or poly acids and wherein the compound of Formula (1) is present at a concentration that provides a dosage of less than about 6 mg/kg/day and the dialdehyde polysaccharide is present at a concentration that provides a dosage of less than about 250 mg/kg/day, wherein the dialdehyde polysaccharide is 40% oxidized cellulose.

* * * * *